(12) United States Patent
Gordon et al.

(10) Patent No.: US 7,591,760 B2
(45) Date of Patent: Sep. 22, 2009

(54) METHOD AND SYSTEM FOR GENERATING AN EXERCISE PROGRAM

(75) Inventors: Stephen L. Gordon, Columbia, MD (US); Bob Filer, Richboro, PA (US); Warren J. Potash, Dresher, PA (US); Marilyn M. Pink, Westlake Village, CA (US)

(73) Assignee: Fitness-Health Incorporating Technology Systems, Inc., Westlake Village, CA (US)

( * ) Notice: Subject to any disclaimer, the term of this patent is extended or adjusted under 35 U.S.C. 154(b) by 287 days.

(21) Appl. No.: 10/851,165

(22) Filed: May 24, 2004

(65) Prior Publication Data

US 2004/0220017 A1    Nov. 4, 2004

Related U.S. Application Data

(63) Continuation of application No. 09/921,134, filed on Aug. 3, 2001, now Pat. No. 6,740,007.

(51) Int. Cl.
*A63B 71/00* (2006.01)

(52) U.S. Cl. ............ 482/8; 482/1; 482/9; 482/900

(58) Field of Classification Search ............ 482/1–9, 482/900–902; 434/247; 600/300, 587
See application file for complete search history.

(56) References Cited

U.S. PATENT DOCUMENTS

| | | | | |
|---|---|---|---|---|
| 5,078,152 A * | 1/1992 | Bond et al. | ............ | 600/587 |
| 5,673,691 A * | 10/1997 | Abrams et al. | ............ | 600/300 |
| 5,706,822 A * | 1/1998 | Khavari | ............ | 600/483 |
| 5,931,763 A * | 8/1999 | Alessandri | ............ | 482/4 |
| 5,976,063 A * | 11/1999 | Joutras et al. | ............ | 482/114 |
| 6,007,459 A * | 12/1999 | Burgess | ............ | 482/4 |
| 6,228,000 B1 * | 5/2001 | Jones | ............ | 482/8 |
| 6,264,582 B1 * | 7/2001 | Remes | ............ | 482/8 |
| 6,296,595 B1 * | 10/2001 | Stark et al. | ............ | 482/91 |
| 6,413,190 B1 * | 7/2002 | Wood et al. | ............ | 482/8 |
| 6,439,893 B1 * | 8/2002 | Byrd et al. | ............ | 434/236 |
| 6,447,425 B1 * | 9/2002 | Keller et al. | ............ | 482/8 |
| 6,635,013 B2 * | 10/2003 | Pfeffer | ............ | 600/300 |
| 6,656,091 B1 * | 12/2003 | Abelbeck et al. | ............ | 482/9 |
| 6,659,946 B1 * | 12/2003 | Batchelor et al. | ............ | 600/300 |
| 6,740,007 B2 * | 5/2004 | Gordon et al. | ............ | 482/9 |
| 6,866,613 B1 * | 3/2005 | Brown et al. | ............ | 482/8 |
| 6,872,187 B1 * | 3/2005 | Stark et al. | ............ | 602/16 |

\* cited by examiner

*Primary Examiner*—Glenn Richman
(74) *Attorney, Agent, or Firm*—Kelly Lowry & Kelley, LLP

(57) ABSTRACT

A method and system provides a customized exercise (conditioning) program for the user using a computer. A plurality of different measurements (parameters) are input using the computer, and based on these measurements, a computer program generates a customized exercise program for the user. In accordance with embodiments of the present invention, the customized exercise program may be specific to conditioning the body or a particular body part of the user, or conditioning the user for a particular sport where both exercise program embodiments may include an optional nutrition plan, or alternatively the nutrition plan may generated independently. Advantageously, the computer program provides an efficient, customized conditioning (exercise) program for the user that enables a great amount of flexibility and convenience for the user.

18 Claims, 5 Drawing Sheets

FIG. 4

Sample Body part coding

10 = upper back, anterior and neck
20 = upper back, posterior
30 = lower back, anterior (abdominals)
40 = lower back, posterior
50 = upper extremity, anterior
60 = upper extremity, posterior
70 = lower extremity, anterior
80 = lower extremity, posterior

Sample Function coding
1 = flexibility/stretching/Range of Motion
2 = strength

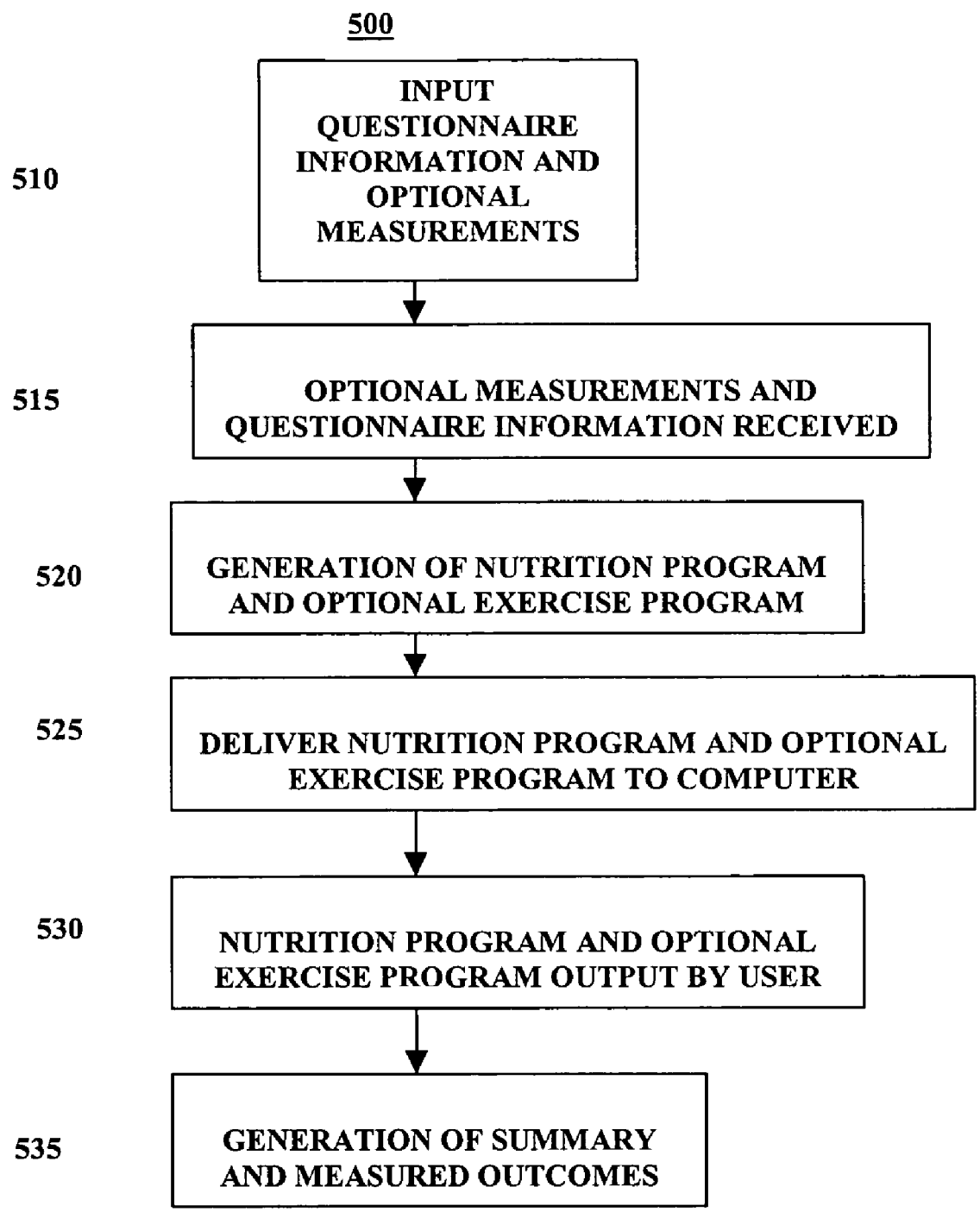

METHOD AND SYSTEM FOR GENERATING AN EXERCISE PROGRAM

RELATED APPLICATIONS

This application is a continuation of U.S. patent application Ser. No. 09/921,134 filed Aug. 3, 2001, now U.S. Pat. No. 6,740,007, which is included herein in its entirety by reference.

BACKGROUND OF THE INVENTION

1. Field of the Invention

The present invention relates generally to exercise systems. It particularly relates to a method and system for generating an exercise program using a computer.

2. Background Art

Getting and staying in shape is a common theme in today's society. Particularly, properly conditioning (exercising) the body or particular body parts is important as people grow older and the body or particular body parts may become more susceptible (vulnerable) to disease or injury. Additionally, many people may get and/or stay in shape by playing a new sport (e.g., tennis), and properly conditioning (training) the body for the particular new sport is important to help avoid injury as body parts (e.g., muscles) perform new functions. Also, optimally (successfully) conditioning the body during these programs may include an associated nutrition plan to help achieve and maintain the optimal weight for the exerciser.

Currently, however, to achieve these goals a user has limited options, none of which offer a great amount of convenience and flexibility to the user. One option is to buy an exercise book that commonly only offers generalized information regarding an exercise program but which cannot offer a customized exercise program. A second option is to go to a healthcare or fitness facility/professional and receive customized, personal guidance that may include high costs and still limits flexibility and convenience to the user. A third option is to try current exercise equipment and software products that offer exercise programs for the user, but are not sport specific nor body or body part specific and also omit a nutrition plan. A fourth option is to try the internet for an interactive customized exercise program, but these programs are essentially the second option over the internet and therefore still limit optimum user convenience and flexibility and do not incorporate nutrition.

Therefore, due to the elements currently missing in the field, there is a need for an efficient process which offers customized exercise programs to a particular user body or body part or to condition the user for a particular sport, and that may optionally include a nutrition plan while still providing a great amount of flexibility and convenience to the user.

SUMMARY OF THE INVENTION

The present invention overcomes the previously mentioned problems by providing a customized exercise (conditioning) program for the user using a computer. A plurality of different measurements (parameters) are input using the computer, and based on these measurements, a computer program generates a customized exercise program for the user. In accordance with embodiments of the present invention, the customized exercise program may be specific to conditioning the body or particular body part of the user, or conditioning the user for a particular sport where both exercise program embodiments may include an optional nutrition plan. Advantageously, the computer program provides an efficient, customized conditioning (exercise) program for the user that enables a great amount of flexibility and convenience for the user.

BRIEF DESCRIPTION OF THE DRAWINGS

FIG. 4 illustrates representative body part coding in accordance with an embodiment of the present invention.

FIG. 5 illustrates a representative flow process diagram for generating an exercise and nutrition program in accordance with an embodiment of the present invention.

DETAILED DESCRIPTION

Figure 1:
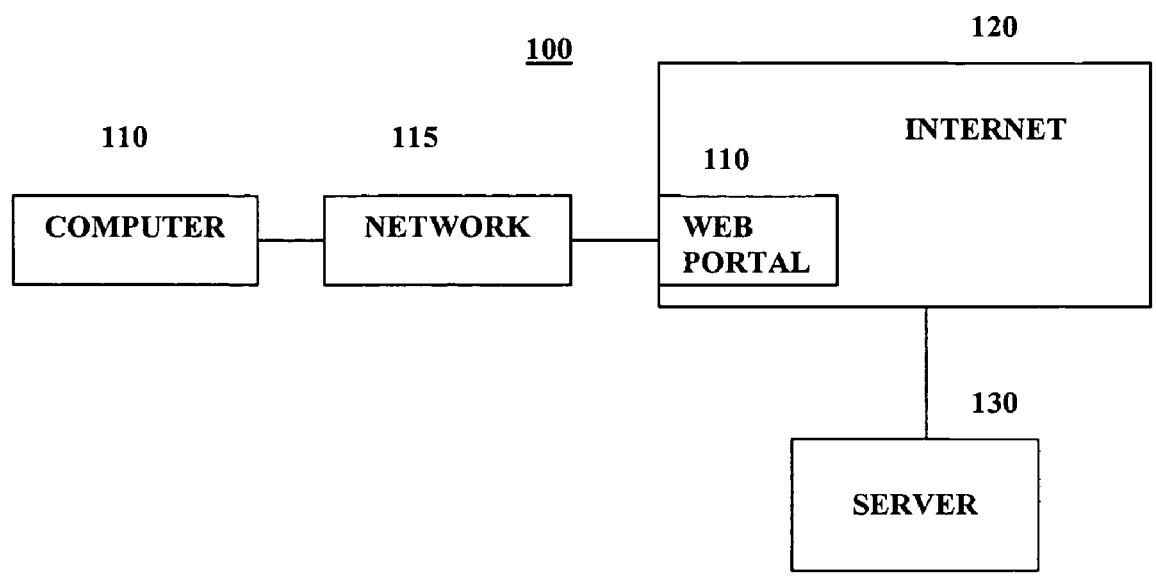
FIG. 1 is a block diagram of an exemplary exercise computer system in accordance with embodiments of the present invention.

FIG. 1 presents a block diagram for the architecture 100 of an exemplary exercise system in accordance with embodiments of the present invention. Computer 110 receives input user measurements and/or parameters from a user (or agent of a user) to generate a customized exercise program for the user. Computer 110 may contain a database to store measurements and set up a profile for each user. Advantageously, computer 110 may interconnect to the internet 120 to deliver the inputted measurements (parameters) via a communications network 115 (e.g., public switched telephone network (PSTN)) or other suitable communications network to interconnect with the internet. These other networks may include, but are not limited to, packet-switched networks, frame relay networks, integrated services digital networks (ISND), cable (broadband) networks, or other networks that interconnect to the internet.

At the internet interface 120, advantageously a web-portal 125 is used to deliver the inputted measurements from the computer 110 to a server 130. The server 130 uses a computer program (algorithm) to generate a customized exercise program for the user. Advantageously, the exercise system may be offered by an application service provider (ASP) that administers the server 130. Also, advantageously, the customized exercise program is specific to conditioning the body or a particular user body part, or specific to conditioning the user for a particular sport. Also, the customized exercise program may optionally include a nutrition portion for improving the user's nutrition and/or maintaining or changing (e.g., gain or loss) the user's weight.

Figure 2:
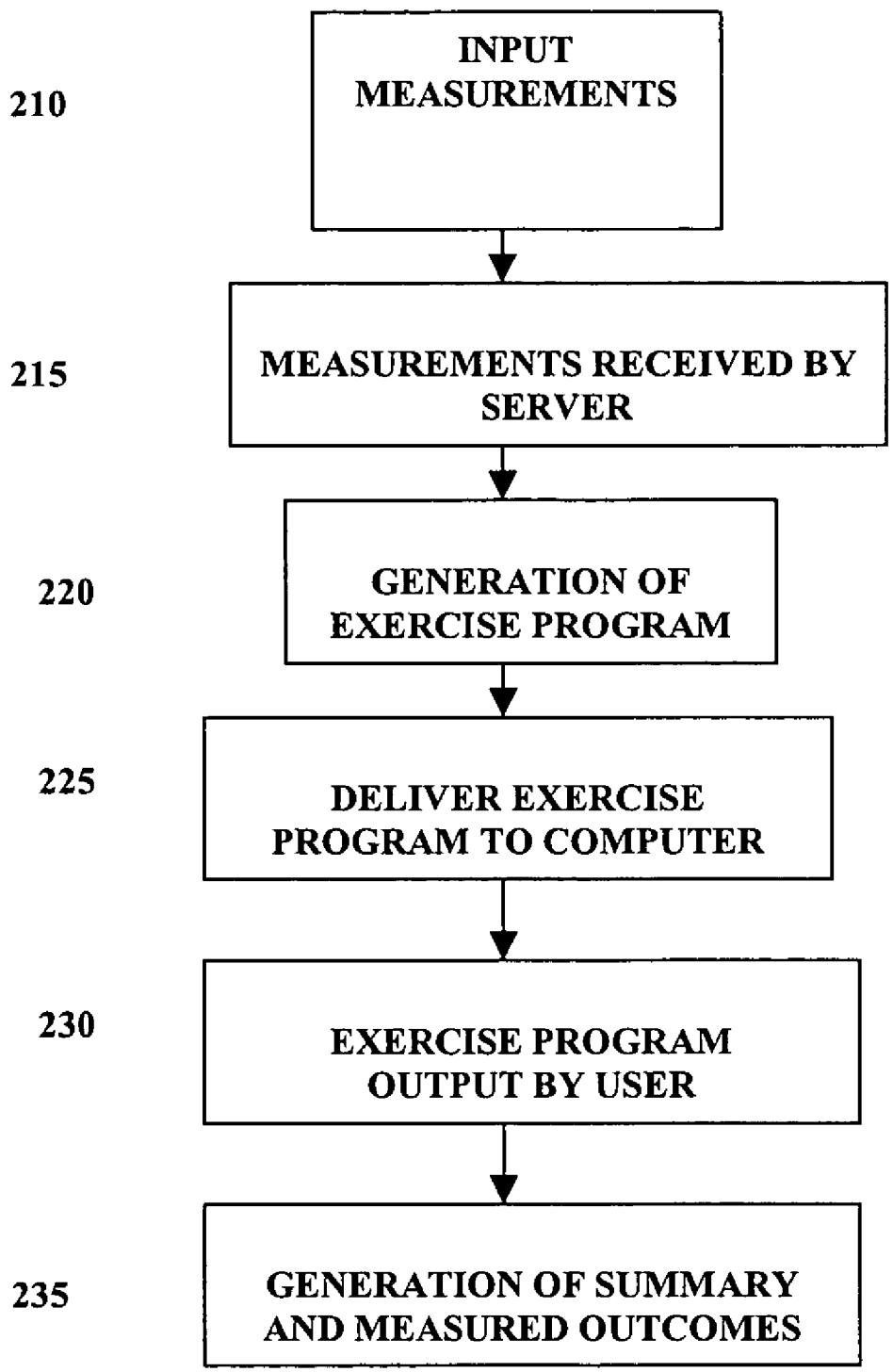
FIG. 2 illustrates a representative flow process diagram for generating an exercise program in accordance with an embodiment of the present invention.

FIG. 2 shows an exemplary flow process diagram 200 followed by the user (or agent of the user) and system 100 in generating a customized exercise program for the user from exercise system architecture 100 in FIG. 1. At step 210, a plurality of user measurements are entered into the computer 110 and contained in a database with a user profile (optionally initiated prior to this step). Prior to this step, the user may choose an exercise program (e.g., body part/system conditioning, particular sport conditioning, etc.) and the server 130, executing a computer program that takes as inputs the exercise program selection and optionally other parameters (user profile and database information, user questionnaire information, etc.), would respond with specific measurements (delivered to computer 110) to be taken of the user (actually exerciser) associated with the selected exercise program. Advantageously, the user or agent may fill out a questionnaire associated with the particular exercise program selected. The questionnaire may include a plurality of user information including, but not limited to, age, gender, and medical history of the user (actual exerciser). After the questionnaire is completed and responses are recorded and submitted to the computer 110, the executed computer program may determine and output the particular measurements to be taken of the user prior to step 210. Then, the user (or agent of the user) would take the necessary measurements as indicated by the server 130. These measurements would be taken and then submitted to the computer at step 210. The user profile and/or questionnaire may include other items relevant to the user.

Additionally, the user profile may contain the user's goals for the exercise program chosen. For example, if the user chose the body or particular body part conditioning program, the user's goal may be to have a spine that is fit and flexible to a certain measurable level. Alternatively, for example, if the user chose the particular sport conditioning program, the user's goal may be to have a certain strength and flexibility in a knee to a certain measurable level that is useful for the particular sport chosen. Also, the user's goals may be performance-driven where, for example, the user's goal is to run a specified distance in a given time-frame (e.g., a five-minute mile). Advantageously, this may be personally done by the user from a user communication device (e.g., from a home or office computer) or done by an agent of the user (e.g., doctor's office employee, employee from user's job, fitness center employee, etc.) at the agent's facility using an agent communications device.

The plurality of user measurements that may be taken and subsequently inputted into the computer advantageously relate to a particular exercise program wanted by the user, either conditioning for a particular sport or conditioning a particular body part. The particular sport chosen may include, but is not limited to, golf, tennis, softball, baseball, swimming, running, soccer, football, basketball, or other sports. The particular body part chosen may include, but is not limited to, the user's spine, pelvis, hip, knee, ankle, foot, shoulder girdle, shoulder, elbow, forearm, wrist, hand, leg, arm, or other user body parts.

The plurality of measurements may include musculoskeletal and/or cardiovascular measurements. The cardiovascular (CV) measurements may include, but are not limited to, heart rate, blood pressure, volume of oxygen, aerobic tests, and other cardiovascular measurements. The musculoskeletal measurements may include, but are not limited to, range of motion (ROM) measurements and strength measurements. Both the ROM and strength measurements may include, but are not limited to, spinal (cervical or lumbar) flexion, spinal extension, spinal rotation, spinal lateral flexion, or hip flexion, hip extension, hip adduction, hip abduction, hip rotation, or knee flexion, knee extension, or ankle plantarflexion, ankle dorsiflexion, or foot inversion, foot eversion, or shoulder flexion, shoulder extension, shoulder rotation, shoulder abduction, shoulder adduction, or elbow flexion, elbow extension, or forearm pronation, forearm supination, or wrist flexion, wrist extension, or other ROM and strength measurements.

As shown in FIG. 2, at step 215, the measurements are sent to and received by the server 130 via the internet web portal 125. At step 220, the customized exercise program is generated based on the measurements input into the computer 110. Also, other parameters, including medical history and the user's goals (objectives) may be combined (assimilated) with the received measurements as a basis for generating the customized exercise program. At step 225, the program is delivered to the computer 110 from server 130. At step 230, the generated exercise program is output by the user (or agent of the user) where the exercise program includes one or more exercises for the user to perform. In accordance with exemplary embodiments of the invention, there are a number of methods for helping the user perform the exercises output by the program including, but not limited to, fitness trainer or user agent assistance, a training manual, or on-line assistance (e.g., live-action video or animation). Advantageously, the output exercise program includes the number of repetitions for each exercise and/or the amount of time each exercise is held (e.g., time to hold a stretch). Also, the exercise program may include the customized period(s) when the user should re-take the earlier measurements to provide an update to the system 100 and generate an updated exercise program (substantially repeating steps 210-230). Also, it may be an option for the user to input which specific exercises were attempted/completed each time the user initiates an exercise session. Therein, the system 100 can log actual performance of the exercise program as particular exercises of the program are completed. Advantageously at step 235, in response to the input measurements and/or updated measurements being input to the computer 110, a summary of the exercise program and measured outcomes (optionally shown by a graph output) are output by the user (or agent of the user). The summary (e.g., in graphical form) of the exercise program may include gains/losses made by the user over some time period and may optionally include the normative data for the user. Advantageously, upon generation of the exercise program, the user begins performance of the program perhaps using the aid of a fitness or healthcare professional.

When an updating process is undertaken and updated exercise programs are output, this summary may be a running summary wherein the exercise program defines (presents) numerically and graphically the relative performance of the user compared to some determined norms. Each time the user performs the exercise program, the user will enter the actual exercises performed into the computer 110 along with any notes. At times that may be specified by the original exercise program output, the user measurements are retaken and input to the computer 110. The computer program (algorithm) then re-assimilates (repeats data analysis) the data, indicates when the user measurements are to be taken again, and updates the exercise program. Again, the changes in performance (e.g., strength and ROM) relative to norms and relative to prior measurements may be presented both numerically and graphically by the executed computer program. When an agent is employed, the updated exercise program may be performed by the user upon verbal and/or visual assistance (instruction) given by the agent. Subsequently, performance (actual completion and/or partial performance of particular exercises) of the program will be input to the computer 110 as exercises are performed.

This updating process may be repeated until conditioning goals (e.g., desired endpoints of the computer program), a pre-determined time period (e.g. 12 weeks), or some other limits are reached by the user. Advantageously, at the conclusion of the program, final measurements are taken and entered into the computer 110. The overall changes in user performance at each measurement session, as compared to norms, are displayed numerically and graphically.

In a typical example, the user may select body/body part conditioning and particularly want to condition his or her spine (e.g., desires a spine conditioning program). Advantageously, a questionnaire associated with a spine conditioning program (e.g., from a database associated with computer 110) is completed by the user (or agent) where the questionnaire includes, but is not limited to the following information: a) contact information, b) date of birth, gender, work status, work loss last three months and last twelve months, c) current pain level (e.g., scale 1-10), duration of pain, location of pain, d) optional current medical care information (e.g., under current medical care? If yes, then type of medical care/practitioner such as MD, Chiropractor, physical therapist—PT, doctor of osteopathic medicine—DO, acupuncturist, herbalist, etc.), e) medical history (e.g., heart disease, blood pressure, smoke—yes/no responses), f) current physical activities (e.g., getting out of bed, standing, sitting 30 minutes, sitting 60 minutes, driving 60 minutes, walking slowly 15 minutes, etc and using a scale of 1-5 from 'not difficult' to 'can't do' associated with each activity).

Subsequently, in accordance with the steps shown in FIG. 2, performance measurements (associated with the spine conditioning program) are taken and entered into computer 110. Advantageously, the performance measurements may be determined and output by the computer program in response to the exercise program user selection (e.g., spine conditioning program) and questionnaire responses. For example, the performance measurements for the spine conditioning program may include, but are not limited to, the following measurements:

a. Range of Motion (ROM)
      i. Lumbar forward flexion, lateral flexion, extension and rotation
      ii. Cervical forward flexion, lateral flexion, extension and rotation
      iii. Hip flexion and extension with knee straight
   b. Strength
      i. Abdominal flexion
      ii. Lumbar extension and rotation
      iii. Cervical forward flexion, lateral flexion, extension and rotation
      iv. Hip extension and flexion Alternatively, prior to following the process shown in FIG. 2, the user may, for example, select the sport conditioning program and particularly select golf conditioning. Advantageously, similar to the body/body part conditioning program, a questionnaire associated with a golf conditioning program (e.g., from a database associated with computer 110) is completed by the user (or agent) where the questionnaire includes, but is not limited to the following information: a) contact information, b) date of birth, gender, c) medical history (heart disease, blood pressure, smoke—yes/no responses), d) golf handicap, e) average number of times played in the last month, number of months user played golf the past year, f) average number of holes played while playing golf, g) number of years played golf (at least 12 rounds per year), h) does user currently work with a golf pro at least once a month (yes/no), i) does user walk the course (yes/no) or use a golf cart (yes/no), j) average number of times user performed strengthening exercises, stretching exercises, and cardiovascular exercises the past month, k) other sports that user performs at least twice a week (list).

Subsequently, in accordance with the steps shown in FIG. 2, performance measurements are taken and entered into computer 110. The performance measurements are specific to each sport selected (e.g., golf conditioning). Also, advantageously, the performance measurements may be determined and output by the computer program in response to the sport program user selection (e.g., golf conditioning program) and questionnaire responses. For example, in golf, the most common injury is to the lower back. This is because of the large degree of ROM required during the swing. Given the large degree of ROM required, trunk stability is vital. Thus, trunk rotation ROM and trunk stability strength are two important measurements that the computer 110 may request. Also in golf, it is proven that the source of power is in the hips (gluteal muscles), thus the strength of that area is one of the selected measurements. Furthermore, in golf, the vast majority of upper extremity injuries are to the lead arm (typically the non-dominate arm). Thus, bilateral strength is important in the upper extremity and may be selected for measurement. For the golf conditioning program, the measurements may include, but are not limited to the following measurements:

a. Range of Motion (ROM)
      i. Lumbar forward flexion, lateral flexion, extension and rotation
      ii. Cervical forward flexion, lateral flexion, extension and rotation
      iii. Hip flexion, extension, rotation, abduction, adduction and flexion with a knee straight (a straight leg raise to measure hamstring length)
      iv. Shoulder flexion, extension, rotation, abduction, horizontal abduction and horizontal adduction
   b. Strength
      i. Abdominal flexion
      ii. Lumbar extension, lateral flexion and rotation
      iii. Cervical forward flexion, lateral flexion, extension and rotation
      iv. Hip extension, flexion, abduction and rotation
      v. Shoulder flexion, extension, rotation, abduction, horizontal abduction and horizontal adduction
      vi. Scapular retraction and protraction
   c. Cardiovascular Conditioning
      i. Harvard step test, or
      ii. Bicycle test, or
      iii. Treadmill test Additionally, for either program that is selected, instructions are included defining how each measurement is to be performed. Subsequently, the user measurements are taken and entered into the computer 110. Advantageously, the measurements are taken and/or recorded as continuous numbers and then converted into ordinal numbers (e.g., scale of 1-5 reflecting poor, fair, good, normal, and excellent ROM and strength) by the computer program. For example, a continuous number may be a ROM measurement such as a shoulder flexion ROM measurement where the shoulder has approximately 180 degrees of flexion (the range being from the arms being down at a person's side to the fingers being pointed at the sky). Also, there is equal distance between continuous numbers such that a person with 90 degrees of flexion has twice the range of a person with 45 degrees of flexion where the flexion ROM number represents a quantifiable measurement. An ordinal number is an assigned number representing where on a relative (qualitative) scale an entity stands. For example, when grouping numbers (e.g., different measurements), in accordance with embodiments of the present invention, a number can be assigned to represent different groups (of measurements), and the number assignment represents a relative order to the groups. As a specific example, if the shoulder only has between 1 and 25 degrees of flexion, an ordinal number of "1" may be assigned to that group, and if the shoulder has between 26 and 50 degrees of flexion, an ordinal number of "2" is assigned, and so on.

Based upon the measurements taken and entered, in accordance with steps shown in FIG. 2, the computer program (algorithm) selects and outputs exercises of varying levels of difficulty. For example, if the abdominal strength were poor, the exercise (delivered by the computer program) may simply be to lie on the back with hips and knees bent and feet flat on the floor (crook lying), hands on the stomach and contract the muscles under the hand while breathing and holding the contraction for a count of 15. Whereas if the abdominal strength were excellent, the algorithm may select an exercise where the user would be crook lying with hands behind the head and curling up until the shoulder blades are off of the ground. In addition to stretching and strengthening exercises for the sport conditioning program, the program may select an aerobic conditioning program.

Advantageously, the exercises are described with words and/or with pictures to the user (e.g., how to do the motion, the number of repetitions and the number of sets, how long to hold the exercise, the number of times per week to do the exercise, etc.) using the computer 110, an agent, or an alternative display device. The measured level of user's function (measurements), relative to norms, are described numerically and graphically. Also, the computer 110 may determine the time period until the next measurement session. Subsequently, the user performs the exercises. Every time he or she does so, he or she (or an agent) may enter the actual exercises performed into the database along with any comments as to ease, difficulty, pain, etc.

Advantageously, at the pre-determined time interval for updated measurements, the computer 110 (using the executed computer program) defines and presents the measurements to be taken (such as the above-mentioned measurements) and the process is repeated. Advantageously, at a pre-determined end-point, the computer 110 (using the executed computer program) defines and presents the final measurements to be taken. Those measurements are taken and entered into the computer 110. The measured levels for each measurement session may be displayed numerically and graphically along with the relative norms.

Figure 3:
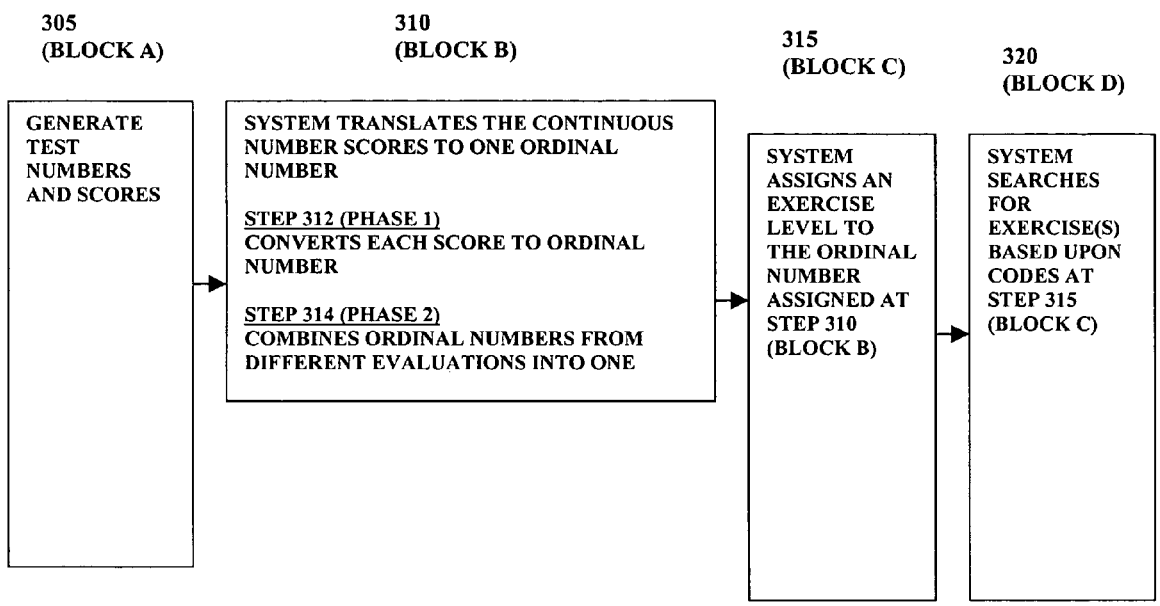
FIG. 3 illustrates a representative detailed flow process diagram for generating an exercise program in accordance with an embodiment of the present invention.

FIG. 3 illustrates the detailed process 300 followed by system 100 by which an exercise/conditioning program may be generated in accordance with an embodiment of the present invention. As previously described, the system 100 selects which measurements are to be taken on the end user (actual exerciser) dependent upon which conditioning program he or she selected. At step 305, these measurements are input to the computer 110 and test numbers and scores are generated from these measurements. In the example of measuring abdominal strength, which may be measured for both body/body part conditioning and particular sport conditioning, the system 100 would first code (or pre-coded) the abdominal body part as '30' and would code the strength function as '2' as shown in FIG. 4. The variables in the T value are T (body part code, function code, and test number) evaluation TEST scores. Evaluation TEST scores would be entered for the variables T(30, 2, 9) (abdominal strength in supine position) and T(30, 2, 21) (abdominal strength with machine testing). The scores for evaluation variable T(30, 2, 9) can range from 0-34, and the scores for evaluation variable T(30, 2, 21) can range from 25-60 for females and from 20-110 for males.

Subsequently, as shown at step 310 (Block B) the system 100 then goes through 2 phases (steps 312 and 314) in translating the continuous number scores on all like body part functions to one ordinal number. In phase one (step 312), the continuous numbers collected for each T variable in Block A are converted to ordinal numbers. For example, if an end user scored between 0 and 9 on test 9 (hence T(30, 2, 9) 0-9), the ordinal number '1' is assigned. If he or she scored 14 on test 9 (hence T(30, 2, 9) 10-14), the ordinal number '2' is assigned.

A list of ordinal assignments to the continuous numbers may be indicated as follows:
T(30,2,9) 0-9=1;
T(30,2,9) 10-14=2;
T(30,2,9) 15-19=3;
T(30,2,9) 20-24=4;
T(30,2,9) 25-34=5;
T(30,2,21F*) 25-30=1;
T(30,2,21F) 30.01-35=2;
T(30,2,21F) 35.01-40=3;
T(30,2,21F) 40.01-50=4;
T(30,2,21F) 50.01-60=5;
T(30,2,21M*) 20-40=1;
T(30,2,21M) 40.01-60=2;
T(30,2,21M) 60.01-70=3;
T(30,2,21M) 70.01-90=4;
T(30,2,21M) 90.01-110=5;
*F=FEMALE
*M=MALE For both tests 9 and 21, there are 5 ordinal numbers on the scale (1-5). The algorithm for converting from continuous variables to ordinal numbers may be accomplished by linear or non-linear formulae.

In phase 2 (step 314) of Block B, the system determines one ordinal number for all the tests done for the one body part function (in this example, the body part function is abdominal strength). So, the system looks to see if the ordinal numbers assigned for tests 9 (T(30, 2, 9)) and 21 (T(30, 2, 21)) are equal. If the numbers are not equal, then the system assigns the number that is the lesser of the numbers.

At step 315 (Block C), the system determines whether the exercise level should be very weak, weak, intermediate, strong or very strong strength muscles (thus translating the 5 ordinal numbers in Block B to exercise levels). If a '1' is assigned in Block C, the exercise level is considered to be for very weak strength muscles, if a '2' is assigned in Block C, the exercise is considered to be for weak strength muscles, if a '3' is assigned in Block C, the exercise level is considered to be for intermediate strength muscles, if a '4' is assigned in Block C, the exercise level is considered to be for strong strength muscles, and if a '5' is assigned in Block C, the exercise level is considered to be for very strong strength muscles.

At step 320 (Block D), the system defines an EXERCISE variable E(30, 2, x) that gives the specific exercise to be used. In the variable E(30, 2, x), x is the difficulty code (ranging from weak difficulty to high difficulty up from a value of "1") computed from the matching ordinal T variables. For a plurality of embodiments for the present invention, there may be several alternative exercises that the computer program may recommend for each body part code, function code, and difficulty code. For example, if T(30, 2, 9)=1 and T(30, 2, 21Female)=1, then the Exercise variable selected by the system is E(30, 2, 1), for example an exercise for weak strength abdominal muscles, would be selected by system 100. For this example, the exercise chosen would be for an isometric abdominal contraction in the crook lying position (supine, knees and hips bent, feet on the floor). In another example, if T(30, 2, 9)=3 and T(30, 2, 21)=4, then the Exercise variable is E(30, 2, 3) and the system selects the exercises for intermediate strength abdominal muscles. There are actually several abdominal exercises available for Exercise variable E(30, 2, 3). For example, there is both a modified bicycle abdominal curl and an intermediate stomach crunch. (The modified bicycle abdominal curl is done in crook lying, the end user places the right foot on the left knee and interlocks the fingers behind the head. A pelvic tilt is done and the right shoulder is raised off of the table so that the right elbow reaches the left knee. An intermediate stomach crunch is also done in crook lying with the fingers interlocked behind the head. The end user then curls up such that the shoulder blade is just off of the table.) When multiple exercises are chosen by the system, the end user or agent may then choose to do one or more of the selected exercises.

Advantageously, the computer program of the server uses the musculoskeletal and cardiovascular measures to actually design and progress the program. How an individual measures on the musculoskeletal and CV parameters determines which exercises are recommended by the program. Advantageously, there may be a plurality of measurements that can be done (dependent upon the goal) and a plurality of exercises in the database from which the program (algorithm) chooses (dependent upon the outcome of the measurement). For example, if the user had excellent quad strength and good hamstring flexibility, certain exercises would be chosen. In contrast, if the user had only fair quad strength and poor hamstring flexibility, different exercises would be chosen.

In an alternative embodiment, the customized exercise program may include a nutrition program portion for improving the user's nutrition and/or maintaining or changing (e.g., gain or loss) the user's weight. Also, the nutrition program may be separate and performed independently from the exercise program. FIG. 5 shows an exemplary flow process diagram 500 followed by the user (or agent of the user) and system 100 in generating a customized nutrition exercise/nutrition program or solely a nutrition program for the user from system architecture 100 in FIG. 1.

Advantageously, the user fills out a nutrition questionnaire which may include food likes/dislikes, relevant medical information (e.g., blood pressure, cholesterol lipids and ratios, etc.), medication, body fat, current weight, recent weight changes, and weight goals (e.g., maintain weight, gain 5 pounds, loose 10 pounds, etc.). For example, the food likes/dislikes may be the food group of 'vegetables'. A list of vegetables may then appear and the user may tick off the individual vegetables as either 'like', 'o.k. in moderation', or 'won't eat'. At step 510, the questionnaire information (answers to the questionnaire), optionally along with the previously described user measurements, are entered into the computer 110 and contained in a database with a user profile (optionally initiated prior to this step). For solely performing the nutrition program, only the questionnaire information is input to the computer 110 at step 510.

As shown in FIG. 5, at step 515, the questionnaire information and optional user measurements are sent to and received by the server 130 via the internet web portal 125. For a nutrition/exercise program embodiment, an exercise program is determined, using server 130, in response to the user measurements. The computer 110, using server 130, then executes a computer program to calculate the required number of calories and dispersion of calories in the food groups based upon the determined exercise program, age, gender, and weight. A template food plan is then determined by the computer 110 using server 130. Alternatively, for generation of an independent nutrition program, an exercise program is not determined and only the questionnaire information, including age, gender, and weight, is used to calculate the required number of calories and dispersion of calories in the food groups for generating the template meal plan. The computer 110, using server 130, may continue to scan the input questionnaire information for medical history and medication to alter the template food plan. For example, if a user noted that she or he were on one of the statin drugs such as Provocal for cholesterol management, all 'grapefruit' choices in the food plan would be replaced with a different fruit (grapefruit is contraindicated with Provocal) using the computer program executed by server 130. The computer 110, using server 130, scans for weight gain/loss goals and then accordingly adjusts the caloric intake. Also the computer program executed by computer 110, using server 130, may scan for food preferences and appropriate substitutes within the food groups. At step 520, a suggested nutritional program and optional exercise program is generated based on the questionnaire information and optional user measurements input into the computer 110.

At step 525, the nutrition program and optional exercise program is delivered to the computer 110 from server 130. At step 530, the generated nutrition program and optional exercise program is output by the user (or agent of the user) where the exercise program (if selected) includes one or more exercises for the user to perform, and the suggested nutrition plan may include a meal plan, recipes, and a shopping list. The meal plan may be for a week, or it may be for the time period until the next user measurement inputs are entered.

Actual food intake may be entered by the user or agent. Progress towards the nutritional goal can be incorporated into the outcome measures previously described with the physiological user measurements to output, at step 535, a summary of the nutrition program (and optional exercise program) and measured outcomes (optionally shown by a graph output), advantageously output by the user (or agent of the user). The summary (e.g., in graphical form) of the nutrition program may include gains/losses made by the user over some time period and may optionally include the normative data for the user.

Additionally, the computer exercise program (optionally including a nutrition program portion) or independent computer nutrition program may be embodied as a machine-readable medium having stored thereon a plurality of executable instructions, the plurality of instructions comprising instructions to perform the steps of the process described herein.

Although the invention is described herein using an Internet example, it will be appreciated by those skilled in the art that modifications and changes may be made without departing from the spirit and scope of the present invention. As such, the method and system described herein may be equally applied to any network allowing a user to generate an exercise program using a computer program.

What is claimed is:

1. A method for creating a computer-generated exercise program for an individual, comprising the steps of:
   accessing a computer program by means of a computer which is not in electronic communication with an exercise or therapy device associated with the individual;
   selecting an activity or one or more body parts to be exercised from a computer-generated menu of options;
   the computer generating a request for musculoskeletal strength measurements, musculoskeletal range of motion measurements or cardiovascular measurements of the individual relating to the activity or body part menu options selected;
   inputting into the computer a response to the request for measurements relating to the individual;
   the computer generating a request for objective parameters of the individual;
   inputting into the computer a response to the request for the individual's objective parameters relating to the selected activity or body part;
   the computer analyzing the individual's objective parameters and measurements input into the computer in relation to the selected activity or one or more body parts to be exercised by means of criteria stored on the computer;

the computer assigning a rank to the individual's measurements or objective parameters; and the computer automatically generating an exercise program for the individual specifically optimized for the selected activity or one or more body parts in relation to the ranking of the individual's measurements or parameters input into the computer.

2. The method of claim 1, further comprising:

generating an update to the exercise program from an updated plurality of individual measurements or parameters being received.

3. The method of claim 1, wherein both the range of motion measurements and strength measurements include either of spinal cervical, spinal lumbar flexion, spinal extension, spinal rotation, spinal lateral flexion, hip flexion, hip extension, hip adduction, hip abduction, hip rotation, knee flexion, knee extension, ankle plantarilexion, ankle dorsiflexion, foot inversion, foot eversion, shoulder flexion, shoulder extension, shoulder rotation, shoulder abduction, shoulder adduction, elbow flexion, elbow extension, forearm pronation, forearm supination, wrist flexion, or wrist extension measurements.

4. The method of claim 1, wherein the individual's measurements are received, a computer program is executed, and the exercise program is generated using a server, interconnected to the internet, and administered by an application service provider.

5. The method of claim 1, wherein the exercise program includes a nutrition portion.

6. The method of claim 1, further comprising:

delivering the exercise program to an agent for the individual at an agent communications device.

7. The method of claim 1, further comprising:

delivering the exercise program to the individual at an individual's communications device.

8. The method of claim 7, wherein the exercise program is delivered to the individual's communications device in response to the individual not being available to receive the exercise program from an agent for the individual using an agent communications device.

9. The method of claim 1, wherein the body part is either of the spine, pelvis, hip, knee, ankle, foot, shoulder girdle, shoulder, elbow, forearm, wrist, hand, leg, or arm of the user.

10. The method of claim 1, wherein the generating a request step includes the step of requesting individual health history parameters.

11. The method of claim 1, wherein the selecting step includes the step of selecting a specific sport activity listed by the computer generated menu.

12. The method of claim 1, including the step of the individual performing at least one exercise of the exercise program without any electronic interface between the device used to perform the at least one exercise and the computer-generated exercise program.

13. The method of claim 12, including the steps of the individual or an agent of the individual inputting performance data of the individual relating to the exercise program or revised objective parameter data into the computer, and the computer generating a new exercise program in response to the input data.

14. The method of claim 13, wherein the performance data includes musculoskeletal strength measurements, musculoskeletal range of motion measurements or cardiovascular measurements of the individual.

15. A method for creating a computer-generated exercise program for an individual, comprising the steps of:

through a network, an individual or an individual's agent accessing a web-site interfacing with a computer program which is not in electronic communication with an exercise or therapy device associated with the individual;

the computer program generating a series of questions to be answered by the individual, including health history questions;

the individual inputting answers to the generated series of questions;

selecting an activity or one or more body parts to be exercised from a computer-generated menu of options of the computer program;

the computer program generating a request for measurements or parameters relating to the individual based on the menu options selected, including at least one of individual objective parameters, musculoskeletal strength measurements of the individual, musculoskeletal range of motion measurements of the individual or cardiovascular measurements of the individual and relating to the selected activity or body part;

inputting into the computer a response to the request for measurements or parameters relating to the individual;

the computer generating a request for individual objective parameters;

the individual inputting the individual's objective parameters relating to the selected activity or body part;

the computer program analyzing the individual's measurements or parameters input into the computer in relation to the selected activity or one or more body parts to be exercised by means of criteria stored on the computer;

the computer assigning a rank to the individual's measurements or parameters;

the computer program automatically generating an exercise program for the individual specifically optimized for the selected activity or one or more body parts in relation to the individual's measurements or parameters input into the computer;

the individual performing at least one exercise of the exercise program without any electronic interface between the device used to perform the at least one exercise and the computer-generated exercise program; and the individual or an agent of the individual inputting performance data of the individual relating to the exercise program or revised objective parameter data into the computer, and the computer generating a new exercise program in response to the input data.

16. The method of claim 15, wherein both the range of motion measurements and strength measurements include either of spinal cervical, spinal lumbar flexion, spinal extension, spinal rotation, spinal lateral flexion, hip flexion, hip extension, hip adduction, hip abduction, hip rotation, knee flexion, knee extension, ankle plantarflexion, ankle dorsiflexion, foot inversion, foot eversion, shoulder flexion, shoulder extension, shoulder rotation, shoulder abduction, shoulder adduction, elbow flexion, elbow extension, forearm pronation, forearm supination, wrist flexion, or wrist extension measurements.

17. The method of claim 15, wherein the exercise program includes a nutrition program automatically generated by the computer program.

18. The method of claim 15, wherein the selecting step includes the step of selecting a specific sports activity listed by the computer generated menu.

* * * * *

UNITED STATES PATENT AND TRADEMARK OFFICE
CERTIFICATE OF CORRECTION

| | | |
|---|---|---|
| PATENT NO. | : 7,591,760 B2 | Page 1 of 1 |
| APPLICATION NO. | : 10/851165 | |
| DATED | : September 22, 2009 | |
| INVENTOR(S) | : Stephen L. Gordon et al. | |

It is certified that error appears in the above-identified patent and that said Letters Patent is hereby corrected as shown below:

In column 11, line 19 (claim 3), replace "plantarilexion" with "plantarflexion".

Signed and Sealed this
Twentieth Day of September, 2011

David J. Kappos
*Director of the United States Patent and Trademark Office*